(12) United States Patent
Gueckel (10) Patent No.: US 7,507,845 B1
(45) Date of Patent: Mar. 24, 2009

(54) PROCESS FOR PRODUCTION OF AN OLEFIN OXIDE

(75) Inventor: Christian J. Gueckel, Paramus, NJ (US)

(73) Assignee: SD Lizenzverwertungsgesellschaft mbH & Co KG, Munich (DE)

( * ) Notice: Subject to any disclaimer, the term of this patent is extended or adjusted under 35 U.S.C. 154(b) by 0 days.

(21) Appl. No.: 11/845,180

(22) Filed: Aug. 27, 2007

(51) Int. Cl.
*C07D 301/10* (2006.01)

(52) U.S. Cl. .................. 549/536; 549/537; 502/348; 502/355; 502/415; 502/64; 502/68; 502/72; 502/80; 502/87

(58) Field of Classification Search .............. 549/536, 549/537; 502/355, 415, 348, 64, 68, 72, 502/80, 87
See application file for complete search history.

(56) References Cited

U.S. PATENT DOCUMENTS

| 3,962,136 A | 6/1976 | Nielsen et al. |
| 4,010,115 A | 3/1977 | Nielsen et al. |
| 4,012,425 A | 3/1977 | Nielsen et al. |
| 4,039,561 A | 8/1977 | Mitsuhata et al. |
| 4,066,575 A | 1/1978 | Winnick |
| 4,350,616 A | 9/1982 | Boussert |
| 4,761,394 A | 8/1988 | Lauritzen |
| 4,766,105 A | 8/1988 | Lauritzen |
| 4,808,738 A | 2/1989 | Lauritzen |
| 4,820,675 A | 4/1989 | Lauritzen |
| 4,833,261 A | 5/1989 | Lauritzen |
| 5,187,140 A * | 2/1993 | Thorsteinson et al. ....... 502/348 |
| 5,935,898 A | 8/1999 | Trübenback et al. |
| 2007/0111886 A1 | 5/2007 | Serafin et al. |
| 2008/0081920 A1* | 4/2008 | Gueckel ..................... 549/533 |

* cited by examiner

*Primary Examiner*—Bernard Dentz
*Assistant Examiner*—David E Gallis
(74) *Attorney, Agent, or Firm*—Scully, Scott, Murphy & Presser, P.C.

(57) ABSTRACT

The invention relates to a process for the epoxidation of an olefin, wherein the concentration of the olefin oxide in the outlet is greater than about 2.2% by volume. More particularly, the invention relates to a process for the epoxidation of ethylene by contacting a feed including at least ethylene and oxygen with an improved epoxidation catalyst. The catalyst which has improved selectivity in the epoxidation process at high productivities, includes a solid support having a surface, which has a first mode of pores that have a diameter ranging from about 0.01 μm to about 5 μm and having a differential pore volume peak in the range from about 0.01 μm to about 5 μm. The surface also has a second mode of pores, which is different from the first mode of pores, having a diameter ranging from about 1 μm to about 20 μm and have a differential pore volume peak in the range from about 1 μm to about 20 μm. On the bimodal pore surface is a catalytically effective amount of silver or a silver-containing compound, a promoting amount of rhenium or a rhenium-containing compound, and a promoting amount of one or more alkali metals or alkali-metal-containing compounds.

20 Claims, 1 Drawing Sheet

PROCESS FOR PRODUCTION OF AN OLEFIN OXIDE

FIELD OF THE INVENTION

The present invention pertains to a process for the epoxidation of an olefin to an olefin oxide by contacting a feed gas comprising an olefin and oxygen with a catalyst comprising a silver compound and a rhenium compound deposited on a carrier with bimodal pore size distribution, wherein the concentration of the olefin oxide in the reactor outlet is greater than about 2.2% by volume. More particularly, the invention pertains to an improved catalyst useful for the epoxidation of ethylene to ethylene oxide at high catalyst work rates.

DESCRIPTION OF THE RELATED ART

Generally, commercially practiced olefin epoxidation is carried out by continuously contacting a feed gas comprising oxygen and an olefin with a catalyst under defined operating conditions. The resulting product mixture of olefin oxide and typically un-reacted oxygen and olefin as well as the total combustion products undergoes a separation procedure wherein the un-reacted feed gas components are separated from the products and undesired by-products.

For economical purposes, it is preferred to operate production plants for olefin oxide at maximum productivity and highest selectivity. In order to maximize the productivity, the catalyst work rate has to be increased which is usually achieved by either raising the flow rate, i.e., Gas Hourly Space Velocity, at fixed olefin oxide concentration at the reactor outlet and/or changing the concentration of the olefin oxide in the reactor outlet by adjusting the olefin and oxygen conversion.

Since all olefin oxide plants have limited capability for increasing the flow rate because of the plant design, the most common procedure to increase the productivity is the adjustment of the olefin oxide concentration in the reactor outlet. In general, the outlet concentration adjustments are achieved in the prior art by increasing the catalyst temperature and thereby increasing the olefin and oxygen conversion. However, by increasing the level of olefin oxide in the reactor outlet, the selectivity of the process decreases significantly which counteracts the desired productivity increasing. Therefore, most plants run at low olefin oxide outlet concentration in order to achieve high selectivites at moderate productivity. By "low olefin oxide outlet concentration", it is meant that the olefin oxide outlet concentration is typically 1.8% v or less.

There is continuing interest in producing improved catalysts for the epoxidation of olefins at higher productivities. In this respect, and of particular interest, are catalysts for the highly selective epoxidation of ethylene since these catalysts are known to lose selectivity significantly at high productivities.

These catalysts typically comprise a porous refractory support such as alpha alumina, which has on its surface a catalytic amount of silver and at least one promoter that helps to increase selectivity in the epoxidation process. The use of alkali metals and transition metals as promoters for silver catalysts is well known for the production of ethylene oxide by the partial oxidation of ethylene in the vapor phase. The catalyst may comprise further elements like alkali metals, as are described in U.S. Pat. Nos. 3,962,136 and 4,010,115. In particular, the '136 and the '115 patents disclose Ag/alkali metal catalysts without rhenium, Re.

Over the last two decades, rhenium was described as being effective in improving the selectivity of alkaline metal promoted silver-based catalyst supported by a refractory porous support. Some references in the art are U.S. Pat. Nos. 4,761,394 and 4,833,261. The further improvement of silver-based catalysts promoted with alkaline metals and rhenium by the use of one of sulfur, Mo, W, and Cr was disclosed, for example, in U.S. Pat. Nos. 4,766,105, 4,820,675 and 4,808,738.

Other examples of catalysts are disclosed, for example, in U.S. Pat. Nos. 4,010,155; 4,012,425; 4,123,385; 4,066,575; 4,039,561 and 4,350,616. Such highly selective catalysts contain, in addition to silver, selectivity-enhancing promoters such as rhenium, molybdenum, tungsten and/or nitrate- or nitrite-forming compounds, as are discussed in U.S. Pat. Nos. 4,761,394 and 4,766,105.

U.S. Patent Application Publication No. 20060009647 A1 discloses a process for the epoxidation of an olefin with a catalyst comprising a silver component deposited on a fluoride-mineralized carrier, wherein the partial pressure of olefin oxide in the product mix is greater than 60 kPa. In addition, this printed publication discloses a similar process utilizing a catalyst comprising a silver component and one or more high-selectivity dopants, wherein the partial pressure of olefin oxide in the product mix is greater than 20 kPa. However, the disclosure of the '647 publication does not teach about the influence of the pore size distribution on the catalyst performance at high productivities.

Beside the chemical composition of a supported silver-based epoxidation catalyst, the physical characteristics of the finished catalyst as well the support have been an integral part of catalyst development. Generally, the silver-based catalyst support shows a characteristic pore volume and pore size distribution. Furthermore, the surface area and the water absorption are well-known characteristics for such catalyst supports. It has now been found that the physical characteristics of the finished catalyst and the impact of the characteristics on the catalyst performance are more complicated than heretofore believed, especially if the catalyst is promoted with rhenium. In addition to the surface area, the pore volume and the pore size distribution, the pattern of the pore size distribution, especially the number and the specific characteristics of different modes, has now been found to have a significant positive impact on the catalyst selectivity. In particular, this effect is especially distinguished when the catalyst is operated at very high work rates, i.e., high levels of olefin oxide production.

In view of the above, there is a continued need for providing new and improved Ag-based epoxidation catalysts that exhibited increased performance at high productivites.

SUMMARY OF THE INVENTION

An increased productivity (expressed herein by the concentration of ethylene oxide in the reactor outlet gas) catalyst containing silver and rhenium supported by a carrier with a bimodal pore size distribution is provided that shows improved performance. The catalyst according to the invention shows a minor loss in selectivity at higher productivities whereas conventional catalysts with monomodal pore size distribution show a significant loss in selectivity at higher productivities.

In particular, the invention provides a process for the epoxidation of an olefin to an olefin oxide which comprises contacting a feed including at least oxygen and an olefin in a reactor with a catalyst that includes a support having a bimodal pore size distribution, a catalytically effective amount of silver or a silver-containing compound, a promoting amount of rhenium or a rhenium-containing compound, and a promoting amount of one or more alkali metals or alkali-metal-containing compounds, said reactor including at least a reactor outlet and said olefin oxide produced by said contacting has a concentration in the reactor outlet that is greater than about 2.2% by volume.

The support having the bimodal pore size distribution that is employed in the present invention includes a pore size distribution with a first mode of pores which has a mean diameter ranging from about 0.01 μm to about 5 μm, and a second mode of pores which has a mean diameter ranging from about 5 μm to about 30 μm.

In some embodiments of the present invention, the olefin oxide concentration in the reactor outlet is greater than about 2.4% by volume. In yet other embodiments of the present invention, the ethylene oxide concentration in the reactor outlet is greater than about 2.6% by volume.

In the present invention, the olefin oxide concentration in the reactor outlet is obtained by adjusting the olefin and oxygen conversion. That is, the olefin oxide concentration in the reactor is obtained by increasing the reaction temperature during the epoxidation reaction. An increase of the reaction temperature has always a negative effect on the catalyst selectivity. This decrease in catalyst selectivity is economically undesired and reduces the benefit of the higher productivity. The selectivity decrease can be significant, i.e., more points of selectivity for less than one point increase of the olefin oxide concentration in the reactor outlet. It was found, that catalysts according to the invention show only a minor selectivity decrease at higher productivities, i.e., higher olefin and oxygen conversion, and, therefore, have a significant economical benefit compared to state of the art catalysts.

The invention also provides a process for the oxidation of ethylene to ethylene oxide which comprises the vapor phase oxidation of ethylene with molecular oxygen in a fixed bed, tubular reactor, in the presence of the aforementioned catalyst. In this aspect of the present invention, the ethylene oxide concentration in the reactor outlet is greater than about 2.2% by volume.

BRIEF DESCRIPTION OF THE DRAWINGS

The sole drawing of the present invention, shows a comparison of catalyst performances for the inventive supported Ag-based catalyst and a prior art Ag-based catalyst in applications in which the ethylene oxide concentration at the reactor outlet was equal or greater than about 2.2.

DETAILED DESCRIPTION OF THE INVENTION

As stated above, the present invention provides a process for the epoxidation of an olefin, preferably ethylene, to an olefin oxide, preferably ethylene oxide, which comprises contacting a feed including at least oxygen and an olefin in a reactor with a catalyst that includes a support having a bimodal pore size distribution, a catalytically effective amount of silver or a silver-containing compound, a promoting amount of rhenium or a rhenium-containing compound, and a promoting amount of one or more alkali metals or alkali-metal-containing compounds, said reactor including at least a reactor outlet and said olefin oxide produced by said contacting has a concentration in the reactor outlet that is greater than about 2.2, preferably greater than about 2.4, more preferably, greater than about 2.6, % by volume.

In the present invention, the olefin oxide concentration in the reactor outlet is obtained by adjusting the olefin and oxygen conversion. That is, the olefin oxide concentration in the reactor is obtained by increasing the reaction temperature during the epoxidation reaction. An increase of the reaction temperature has always a negative effect on the catalyst selectivity. This decrease in catalyst selectivity is economically undesired and reduces the benefit of the higher productivity. The selectivity decrease can be significant, i.e., more points of selectivity for less than one point increase of the olefin oxide concentration in the reactor outlet. It was found, that catalysts according to the invention show only a minor selectivity decrease at higher productivities, i.e., higher olefin and oxygen conversion, and, therefore, have a significant economical benefit compared to state of the art catalysts.

The support employed in this invention may be selected from a large number of solid, refractory supports that may be porous and may provide the preferred pore structure. Alumina is well known to be useful as a catalyst support for the epoxidation of an olefin and is the preferred support. The alumina support may also contain various impurities and additives that may or may not influence the catalytic epoxidation reaction. In the process of making the preferred alumina support, high-purity aluminum oxide, preferably alpha-alumina, is thoroughly mixed with temporary and permanent binders. The temporary binders, known as burnout materials, are thermally decomposable organic compounds of moderate to high molecular weight which, on decomposition, alter the pore structure of the support. The permanent binders are typically inorganic clay-type materials having fusion temperatures below that of the alumina and impart mechanical strength to the finished support. After thorough dry-mixing, sufficient water and/or other suitable liquid is added to help form the mass into a paste-like substance. Catalyst support particles are formed from the paste by conventional means such as extrusion. The particles are then dried and are subsequently calcined at an elevated temperature.

The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The preferred support is comprised of alpha-alumina having a very high purity; i.e., at least 95 wt. % pure, or more preferably, at least 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

The solid support employed in the present invention has a bimodal pore size distribution. More particular, the solid support employed in the present invention has a surface including a first mode of pores which have a mean diameter ranging from about 0.01 μm to about 5 μm. Preferably, the first mode of pores has a mean diameter ranging from about 0.1 μm to about 4 μm. The surface of solid support employed in the present invention also has a second mode of pores which is different from the first mode of pores. In particular, the second mode of pores has a mean diameter ranging from about 5 μm to about 30 μm. Preferably, the second mode of pores has a mean diameter ranging from about 5 μm to about 20. Typically, but not necessarily always, the first mode of pores comprises from about at most about 50% of the total pore volume and the second mode provides at least about 50% of the total pore volume. In another embodiment, the first mode of pores comprises at most about 45% of the total pore volume and the second mode provides at least about 55% of the total pore volume. It is believed, without limiting the scope of the invention, that a catalyst with the described bimodal pore size distribution provides advantageous pore structure with reaction chambers separated by diffusion channels.

The final support typically, but not necessarily always, has a water absorption value ranging from about 0.2 cc/g to about 0.8 cc/g, preferably from about 0.25 cc/g to about 0.6 cc/g. The BET surface area of the finished support is preferred to be in the range from about 0.3 to about 4.0 m$^2$/g, more preferably from about 0.3 to about 1.5 m$^2$/g, and most preferably from about 0.3 m$^2$/g to about 1 m$^2$/g. Suitable porosity volumes measured by mercury intrusion techniques are generally in the range from about 0.2 ml/g to about 0.8 ml/g, and preferably from about 0.25 ml/g to about 0.60 ml/g.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The type of reactor is not limited as long as it is capable of producing an olefin oxide by the catalytic oxidation of an olefin. Desirably, the support particles may have equivalent diameters in the range from about 3 mm to about 12 mm, and preferably in the range from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In general and as briefly mentioned above, a suitable catalyst support of the present invention can be prepared by mixing the refractory material, such as alumina, water or other suitable liquid, a burnout material or suitable porosity-controlling agent, and a binder. Burnout materials include cellulose, substituted celluloses, e.g., methylcellulose, ethylcellulose, and carboxyethylcellulose, stearates, such as organic stearate esters, e.g., methyl or ethyl stearate, waxes, granulated polyolefins, particularly polyethylene and polypropylene, walnut shell flour, and the like which are decomposable at the firing temperatures used in preparation of the support. The burnout material is used to modify the porosity of the support and it is essentially totally removed during the firing to produce the finished support. Supports of the present invention are preferably made with the inclusion of a bonding material such as silica with an alkali metal compound in sufficient amount to substantially prevent the formation of crystalline silica compounds. Appropriate binders include inorganic clay-type materials. For instant, a particularly convenient binder material is a mixture of boehmite, an ammonia stabilized silica sol, and a soluble sodium salt.

A paste is formed by mixing the dry ingredients of the support with water or another suitable liquid, and the paste is usually extruded or molded into the desired shape, and then fired or calcined at a temperature from about 1200° C. to about 1600° C. to form the support. When the particles are formed by extrusion, it may be desirable to also include extrusion aids. The amounts of extrusion aids required would depend on a number of factors that relate to the equipment used. However these matters are well within the general knowledge of a person skilled in the art of extruding ceramic materials. After firing, the support is preferably washed to remove soluble residues. Washing is most commonly done with water, but washing with other solvents or aqueous/nonaqueous solutions can also be beneficial.

Suitable supports having a bimodal pore size distribution are available from Saint-Gobain Norpro Co., Sud Chemie AG, Noritake Co., CeramTec AG, and Industrie Bitossi S.p.A.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, based on the total weight of the catalyst including the support. The silver is deposited upon the surface and throughout the pores of a porous refractory support. Silver contents, expressed as metal, from about 1% to about 40% based on the total weight of the catalyst are preferred, while silver contents from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C., preferably from about 200° C. to about 500° C., and more preferably from about 200° C. to about 450° C., at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or stepwise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Non-limiting examples include nitrogen, argon, krypton, helium, and combinations thereof, with the preferred inert gas being nitrogen. Non-limiting examples of the oxygen-containing oxidizing component include molecular oxygen ($O_2$), $CO_2$, NO, $NO_2$, $N_2O$, $N_2O_3$, $N_2O_4$, or $N_2O_5$, or a substance capable of forming NO, $NO_2$, $N_2O$, $N_2O_3$, $N_2O_4$, or $N_2O_5$ under the calcination conditions, or combinations thereof, and optionally comprising $SO_3$, $SO_2$ or combinations thereof. Of these, molecular oxygen is a useful embodiment, and a combination of $O_2$ with NO or $NO_2$ is another useful embodiment. In a useful embodiment, the atmosphere comprises from about 10 ppm to about 1% by volume of an oxygen-containing oxidizing component. In another useful embodiment, the atmosphere comprises from about 50 ppm to about 500 ppm of an oxygen-containing oxidizing component.

In another embodiment, the impregnated support, which has been calcined as disclosed above, may optionally thereafter be contacted with an atmosphere comprising a combination of oxygen and steam, which atmosphere is substantially absent of an olefin, and preferably, completely absent of an olefin. The atmosphere usually comprises from about 2% to about 15% steam by volume, preferably from about 2% to about 10% steam by volume, and more preferably from about 2% to about 8% steam by volume. The atmosphere usually comprises from about 0.5% to about 30% oxygen by volume, preferably from about 1% to about 21% oxygen by volume, and more preferably from about 5% to about 21% oxygen by volume. The balance of the gas atmosphere may be comprised of an inert gas. Non-limiting examples of the inert gas include nitrogen, argon, krypton, helium, and combinations thereof, with the preferred inert gas being nitrogen. The contacting is usually conducted at a temperature from about 200° C. or higher. In one embodiment the contacting is conducted at a temperature from about 200° C. to about 350° C. In another embodiment the contacting is conducted at a temperature from about 230° C. to about 300° C. In another embodiment the contacting is conducted at a temperature from about 250° C. to about 280° C. In another embodiment the contacting is conducted at a temperature from about 260° C. to about 280° C. Usually the contacting is conducted for from about 0.15 hour or more. In one embodiment, the contacting is conducted for from about 0.5 hour to about 200 hours. In another embodiment, the contacting is conducted for from about 3 hours to about 24 hours. In another embodiment, the contacting is conducted for from about 5 hours to about 15 hours.

Olefin Oxide Production

The epoxidation process may be carried out by continuously contacting an oxygen-containing gas with an olefin, which is preferably ethylene, in the presence of the catalyst produced by the invention. Oxygen may be supplied to the reaction in substantially pure molecular form or in a mixture such as air. Molecular oxygen employed as a reactant may be obtained from conventional sources. By way of example, reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers such as organic halides. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount from about 0.3 to about 20 ppmv, and preferably from about 1 to about 15 ppmv of the total volume of the feed gas.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactant, and byproducts to exit the reactor chamber.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1 to about 5 seconds. The present catalysts are effective for this process when operated within these ranges of conditions.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide. In the recycle mode, carbon dioxide concentrations in the gas inlet to the reactor may be, for example, from about 0.3 to about 5 volume percent.

The inventive catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition at the reactor inlet may typically comprises 1-40% ethylene, 3-12% $O_2$, 0.3-40% $CO_2$, 0-3% ethane, 0.3-20 ppmv total concentration of organic chloride moderators, and the balance of the feed being comprised of argon, methane, nitrogen or mixtures thereof.

The following non-limiting examples serve to illustrate the invention.

EXAMPLES

Aluminum Oxides

The following aluminas designed as A and B in Table 1 were used for the preparation of the catalysts. The different types of alumina supports are commercially available.

TABLE I

Physical characteristics of supports

| Support | Water absorption [cc/g] | Total pore volume[a] [cc/g] | Surface area[b] [m²/g] | Mode 1 Mean Pore Diameter [μm] | Mode 1 Pore volume [%]* | Mode 2 Mean Pore Diameter [μm] | Mode 2 Pore volume [%]* |
|---|---|---|---|---|---|---|---|
| A | 0.45 | 0.41 | 0.6 | 0.7 | 25 | 15.8 | 75 |
| B | 0.40 | 0.39 | 1.0 | monomodal distribution | | | |

[a]Mercury intrusion data to 44.500 psia using Micrometrics AutoPore IV 9500 (140° contact angle, 0.480 N/m surface tension of mercury)
[b]Determined according to the Method of Brunauer, Emmet and Teller
*Percentage of the total pore volume of the catalyst Catalyst Preparation
Silver Solution An 834 g portion of silver oxide (Sigma Aldrich) was added to a stirred solution of 442 g oxalic acid dehydrate (ACS Certified Reagent, Fisher) in about 2,800 g deionized water. A precipitate of hydrated silver oxalate salt formed on mixing. Stirring was continued for 0.5 hours. The precipitate was then collected on a filter and washed with deionized water. Analysis showed that the precipitate contained 50.5 wt % silver. Next, 213.9 g of the silver oxalate precipitate was dissolved in a mixture of 77.2 grams ethylenediamine (99+%, Aldrich) and 60.3 g deionized water. The temperature of the solution was kept below 40° C. by combining the reagents slowly, and by cooling the solution. After filtration, the solution contained roughly 30 wt % silver, and had a specific gravity of 1.52 g/mL.

Example 1

Catalyst A

A 150 g portion of alumina support A was placed in a flask and evacuated to approximately 0.1 torr prior to impregnation. To the above silver solution aqueous solutions of cesium hydroxide, perrhenic acid, and ammonium sulfate were added in order to prepare a catalyst composition according to examples 3-10 through 7-20 of U.S. Pat. No. 4,766,105. After thorough mixing, the promoted silver solution was aspirated into the evacuated flask to cover the carrier while maintaining the pressure at approximately 0.1 torr. The vacuum was released after about 5 minutes to restore ambient pressure, hastening complete penetration of the solution into the pores. Subsequently, the excess impregnation solution was drained from the impregnated carrier. Calcination of the wet catalyst was done on a moving belt calciner. In this unit, the wet catalyst is transported on a stainless steel belt through a multi-zone furnace. All zones of the furnace are continuously purged with pre-heated, ultra-high purity nitrogen and the temperature is increased gradually as the catalyst passes from one zone to the next. The heat is radiated from the furnace walls and from the preheated nitrogen.

In this example the wet catalyst entered the furnace at ambient temperature. The temperature was then increased gradually to a maximum of about 450° C. as the catalyst passed through the heated zones. In the last (cooling) zone, the temperature of the now activated was immediately lowered to less than 100° C. before it emerged into ambient atmosphere. The total residence time in the furnace was approximately 45 minutes.

Example 2

Catalyst B (Comparative Example)

Catalyst B was prepared with alunina support B following the procedure of Catalyst A.

Testing of the Catalyst

For testing, the catalyst was charged into a fixed-bed stainless steel tube reactor (¼ inch approximate inner diameter), which was embedded in a heated copper block. The catalyst charge consisted of 12 g crushed catalyst (1.0-1.4 mm particle size) and the inlet gas flow was adjusted to 0.75 Nl/min. The feed gas composition by volume was 25% ethylene, 7% oxygen, 2% carbon dioxide, 0.5-5 ppmv ethyl chloride, and nitrogen ballast. Reaction pressure was maintained at 300 psig. The reactor effluent was analyzed by mass spectrometry at roughly 1-hour intervals.

The feed gas was introduced at 200° C. and increased by 1° C./h until the EO concentration in the reactor outlet reached 3.8% by volume. The ethyl chloride concentration in the inlet gas was adjusted until the maximum selectivity was achieved. Subsequently, the EO concentration in the outlet was lowered to 3% by volume and the ethyl chloride concentration re-adjusted until peak selectivity was observed. Finally, this procedure was repeated at an EO outlet concentration of 2.2% by volume.

TABLE II

Test results

| EO concentration [% v] | Catalyst A Selectivity [% mole] | Catalyst A Temperature [° C.] | Catalyst B* Selectivity [% mole] | Catalyst B* Temperature [° C.] |
|---|---|---|---|---|
| 3.8 | 90.0 | 248 | 86.4 | 244 |
| 3 | 90.9 | 240 | 88.0 | 242 |
| 2.2 | 92.0 | 236 | 89.8 | 239 |

*For comparison

Figure 1:
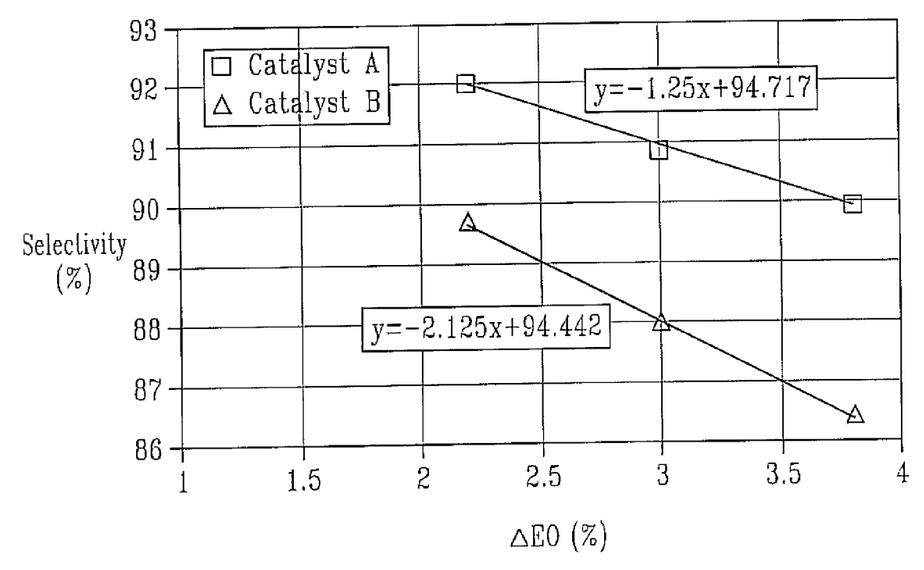

The sole drawing clearly shows that although the catalysts have similar intrinsic selectivites, i.e., the selectivity at 0% ethylene and oxygen conversion, the catalyst according to the invention has a significant lower selectivity decrease towards higher conversion rates expressed by the EO concentration at the reactor outlet.

Porosities are determined by the mercury porosimeter method; see Drake and Ritter, "Ind. Eng. Chem. anal. Ed.," 17, 787 (1945). The pore size distribution is determined by plotting the pores diameter (μm or Angstrom) against the differential pore volume ($ml_{Hg}$/g/pore diameter).

The specific surface area is determined according to the BET method: See J. Am. Chem. Soc. 60, 3098-16 (1938).

While the present invention has been demonstrated and described with reference to preferred embodiments, it will be readily appreciated by those of ordinary skill in the art that various changes and modifications may be made without departing from the spirit and scope of the invention. It is therefore intended that the claims be interpreted to cover the disclosed embodiment, those alternatives which have been discussed, and any and all equivalents thereto.

What is claimed is:

1. A process for the epoxidation of an olefin to an olefin oxide comprising:
    contacting a feed including at least oxygen and an olefin in a reactor with a catalyst that includes a support having a bimodal pore size distribution, with a first mode of pores having a mean diameter ranging from about 0.01 μm to about 5 μm and a second mode of pores having a mean diameter ranging from about 5 μm to about 30 μm, a catalytically effective amount of silver or a silver-containing compound, a promoting amount of rhenium or a rhenium-containing compound, and a promoting amount of one or more alkali metals or alkali-metal-containing compounds, said reactor including at least a reactor outlet and said olefin oxide produced by said contacting has a concentration in the reactor outlet that is greater than about 2.2% by volume.

2. A process for the epoxidation of an olefin to an olefin oxide comprising:
    contacting a feed including at least oxygen and an olefin in a reactor with a catalyst that includes a support having a bimodal pore size distribution, with a first mode of pores having a mean diameter ranging from about 0.1 μm to about 4 μm and a second mode of pores having a mean diameter ranging from about 5 μm to about 20 μm, a catalytically effective amount of silver or a silver-containing compound, a promoting amount of rhenium or a rhenium-containing compound, and a promoting amount of one or more alkali metals or alkali-metal-containing compounds, said reactor including at least a reactor outlet and said olefin oxide produced by said contacting has a concentration in the reactor outlet that is greater than about 2.2% by volume.

3. The process of claim 1 wherein the first mode of pores comprises at most 50% of a total pore volume and the second mode of pores comprises at least 50% of the total pore volume.

4. The process of claim 1 wherein the first mode of pores comprises at most 40% of a total pore volume and the second mode comprises at least 60% of the total pore volume.

5. The process of claim 1 wherein the support comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof.

6. The process of claim 1 wherein the support comprises alumina.

7. The process of claim 1 wherein the support comprises alumina with a surface area of less than about 1 $m^2$/g.

8. The process of claim 1 wherein said catalyst further comprises a promoting amount of one or more Group IIA metal-containing compounds, one or more transition metal-containing compounds, one or more sulfur-containing compounds, one or more fluorine-containing compounds, one or more phosphorus-containing compounds, one or more boron-containing compounds, or combinations thereof.

9. The process of claim 8 wherein the Group IIA metal-containing compound comprises beryllium, magnesium, calcium, strontium, barium or combinations thereof.

10. The process of claim 8 wherein the transition metal-containing compound comprises an element selected from Groups IVA, VA, VIA, VIIA and VIIIA of the Periodic Table of the Elements, or combinations thereof.

11. The process of claim 8 wherein the transition metal-containing compound comprises molybdenum, tungsten, chromium, titanium, hafnium, zirconium, vanadium, thorium, tantalum, niobium or combinations thereof.

12. The process of claim 8 wherein the transition metal-containing compound comprises molybdenum or tungsten or combinations thereof.

13. The process of claim 1 wherein the alkali metal-containing compound comprises lithium, sodium, potassium, rubidium, cesium or combinations thereof.

14. The process of claim 1 wherein the alkali metal-containing compound comprises cesium.

15. The process of claim 1 wherein said olefin is ethylene and said olefin oxide is ethylene oxide.

16. The process of claim 1 wherein said olefin oxide concentration is obtained by adjusting conversion of said olefin and oxygen.

17. The process of claim 16 wherein said adjusting is achieved by increasing the reaction temperature of said epoxidation.

18. The process of claim 1 wherein said reactor is a fixed bed, tubular reactor.

19. The process of claim 1 wherein said contacting is conducting in a vapor phase and said oxygen includes molecular oxygen.

20. A process for the epoxidation of an olefin to an olefin oxide comprising:
    contacting a feed including at least oxygen and an olefin in a reactor with a catalyst that includes a support having a bimodal pore size distribution, with a first mode of pores having a mean diameter ranging from about 0.01 μm to about 5 μm and a second mode of pores having a mean diameter ranging from about 5 μm to about 30 μm, a catalytically effective amount of silver or a silver-containing compound, and a promoting amount of rhenium or a rhenium-containing compound, cesium, lithium, tungsten and sulfur, said reactor including at least a reactor outlet and said olefin oxide produced by said contacting has a concentration in the reactor outlet that is greater than about 2.2% by volume.

* * * * *

(12) INTER PARTES REEXAMINATION CERTIFICATE (759th)
United States Patent
Gueckel (10) Number: US 7,507,845 C1
(45) Certificate Issued: Dec. 9, 2013

(54) PROCESS FOR PRODUCTION OF AN OLEFIN OXIDE

(75) Inventor: Christian J. Gueckel, Paramus, NJ (US)

(73) Assignee: SD Lizenzverwertungsgesellschaft mbH & Co. KG, Munich (DE)

Reexamination Request:
No. 95/001,445, Sep. 13, 2010

Reexamination Certificate for:
Patent No.: 7,507,845
Issued: Mar. 24, 2009
Appl. No.: 11/845,180
Filed: Aug. 27, 2007

(51) Int. Cl.
*C07D 301/10* (2006.01)
*B01J 23/68* (2006.01)
*B01J 35/10* (2006.01)
*B01J 21/04* (2006.01)
*B01J 37/02* (2006.01)

(52) U.S. Cl.
CPC .............. *B01J 23/688* (2013.01); *B01J 35/109* (2013.01); *B01J 21/04* (2013.01); *B01J 35/1009* (2013.01); *B01J 35/1038* (2013.01); *B01J 37/0203* (2013.01)
USPC ........... 549/536; 502/348; 502/355; 502/415; 502/64; 502/68; 502/72; 502/80; 502/87; 549/537

(58) Field of Classification Search
None
See application file for complete search history.

(56) References Cited

To view the complete listing of prior art documents cited during the proceeding for Reexamination Control Number 95/001,445, please refer to the USPTO's public Patent Application Information Retrieval (PAIR) system under the Display References tab.

*Primary Examiner* — Dwayne Jones (57) ABSTRACT

The invention relates to a process for the epoxidation of an olefin, wherein the concentration of the olefin oxide in the outlet is greater than about 2.2% by volume. More particularly, the invention relates to a process for the epoxidation of ethylene by contacting a feed including at least ethylene and oxygen with an improved epoxidation catalyst. The catalyst which has improved selectivity in the epoxidation process at high productivities, includes a solid support having a surface, which has a first mode of pores that have a diameter ranging from about 0.01 μm to about 5 μm and having a differential pore volume peak in the range from about 0.01 μm to about 5 μm. The surface also has a second mode of pores, which is different from the first mode of pores, having a diameter ranging from about 1 μm to about 20 μm and have a differential pore volume peak in the range from about 1 μm to about 20 μm. On the bimodal pore surface is a catalytically effective amount of silver or a silver-containing compound, a promoting amount of rhenium or a rhenium-containing compound, and a promoting amount of one or more alkali metals or alkali-metal-containing compounds.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-35 are cancelled.

\* \* \* \* \*